Figure 1:
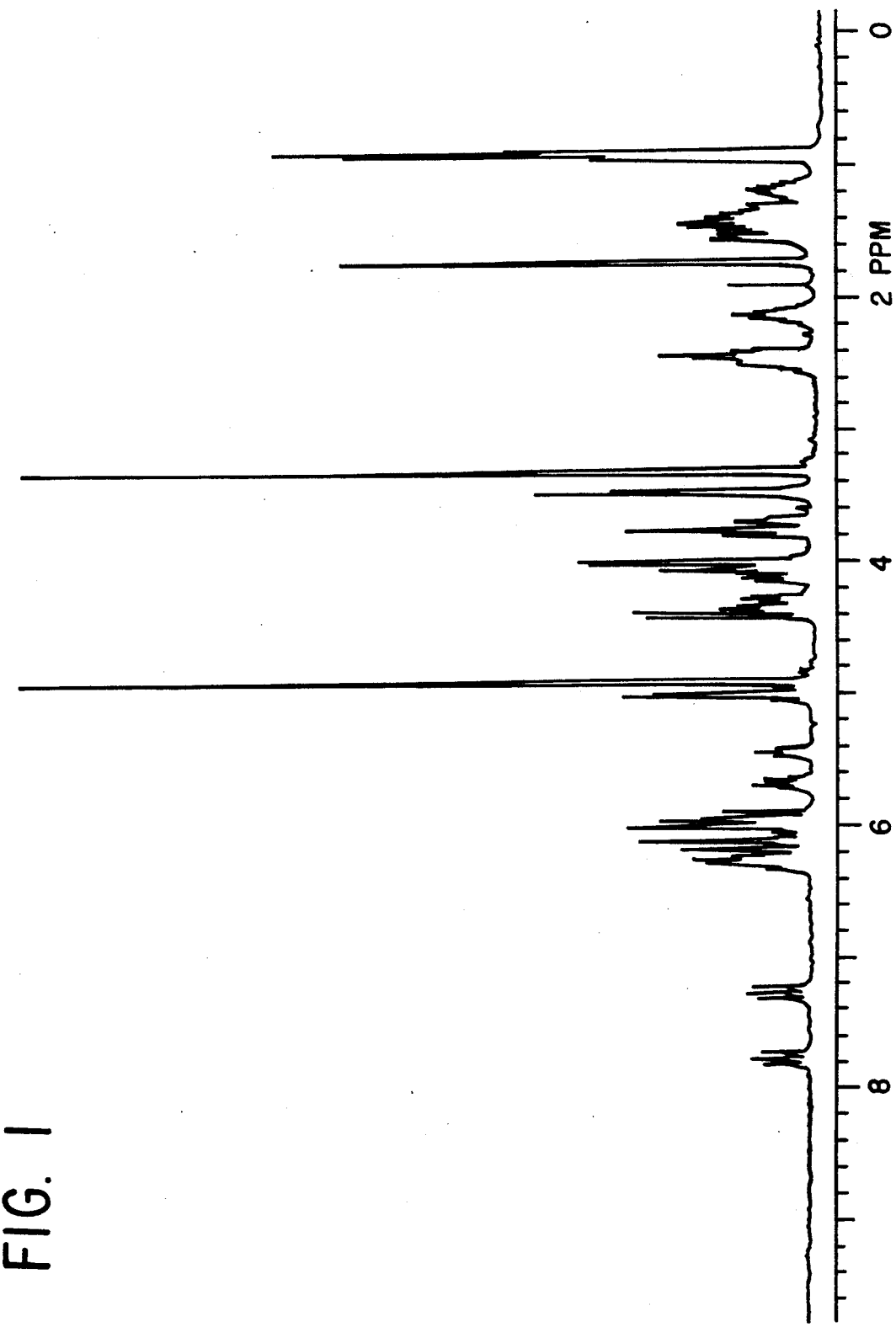

United States Patent [19]

Garrity et al.

[11] Patent Number: 5,091,413

[45] Date of Patent: Feb. 25, 1992

[54] ANTIBIOTIC AGENT

[75] Inventors: George M. Garrity, Westfield, N.J.; Sagrario M. Del Val, Madrid, Spain; Mary Nallin, Westfield, N.J.; Dennis M. Schmatz, Cranford, N.J.; Jack L. Smith, Colonia, N.J.; Frank L. VanMiddlesworth, Fanwood, N.J.; Kenneth E. Wilson, Westfield, N.J.; Marcia M. Zweerink, Shrewsbury, N.J.

[73] Assignee: Merck & Co., Inc., Rahway, N.J.

[21] Appl. No.: 479,482

[22] Filed: Feb. 13, 1990

[51] Int. Cl.$^5$ .................. A61K 31/35; C07D 309/10
[52] U.S. Cl. ......................... 514/460; 549/344; 536/119; 536/16.8; 536/4.1; 514/27
[58] Field of Search ............... 549/344; 514/460, 27; 536/16.8, 119, 4.1

[56] References Cited

U.S. PATENT DOCUMENTS

| 4,251,517 | 2/1981 | Traxler et al. | 536/119 |
| 4,278,665 | 7/1981 | Traxler et al. | 536/4 |
| 4,374,129 | 2/1983 | Traxler et al. | 536/16.8 |

OTHER PUBLICATIONS

Traxler et al., J. Antibiotics, 30(4), 289–296 (1977).
Traxler et al., ibid, 33(9), 967–978 (1977).
Rommele et al., ibid, 36(11), 1539–1542 (1983).
Komori et al., ibid, 38(4), 455–459 (1985).
Komori et al., ibid, 38 (4), 544–546 (1985).
Traxler et al., ibid, 40 (8), 1146–1164 (1987).
Baguley et al., Eur. J. Biochem., 97, 345–351 (1979).
Matsumoto et al., J. Protozool., 36(1), 215–225 (1989).

Primary Examiner—Nicky Chan
Attorney, Agent, or Firm—Alice O. Robertson; Hesna J. Pfeiffer

[57] ABSTRACT

An antibiotic agent produced by the cultivation of *Dictyochaeta simplex* is described. The compound has broad antifungal activity and *antipneumocystis* activity.

9 Claims, 1 Drawing Sheet

ANTIBIOTIC AGENT

DESCRIPTION OF THE INVENTION

According to the present invention, there has been discovered a new product on the cultivation of *Dictyochaeta simplex* which is useful as an antifungal agent and as an antipneumocystis agent. The new product may be represented by the formula

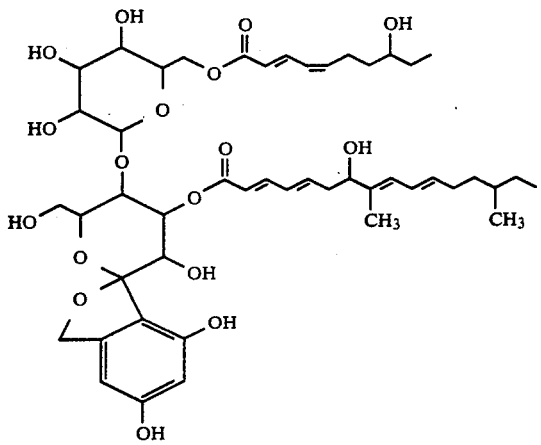

and may be named according to the Chemical Abstracts name of 3',4',5',6'-tetrahydro-3',5,7-trihydroxy-6'-(hydroxymethyl)-5'-[[tetrahydro-3,4,5-trihydroxy-6-[[(8-hydroxy-1-oxo-2,4-decadienyl)oxy]methyl]-2H-pyran-2-yl]oxy]spiro[isobenzofuran-1(3H),2'-[2H]puyran-4'-yl]7-hydroxy-8,14-dimethyl-2,4,8,10-hexadecatetraenoate.

The compound is a white solid characterized by the following physical properties.

NMR Spectral Data

The $^{13}$C-NMR spectrum was recorded at 75 MHz in CD$_3$OD on a Varian XL 300 spectrometer. Chemical shifts given in ppm relative to tetramethylsilane (TMS) at zero ppm are as follows: 169.0, 168.4, 161.6, 154.5, 146.0, 145.5, 143.0, 141.6, 141.3, 137.5, 136.2, 131.5, 127.6, 127.1, 127.1, 121.9, 121.6, 116.4, 111.9, 105.3, 103.0, 100.0, 77.6, 77.6, 76.3, 74.8, 74.6, 74.0, 73.9, 73.2, 72.5, 71.8, 70.4, 64.9, 61.5, 40.0, 37.5, 37.5, 35.2, 31.6, 31.1., 30.4, 25.9, 19.5, 12.2, 11.7, 10.4.

The $^1$H-NMR spectrum was recorded at 300 MHz in CD$_3$OD on the same instrument and is seen in FIG. 1.

Infrared Spectral Data

The IR spectrum as a film on a ZnSe multiple internal reflectance (MIR) crystal was obtained using a Perkin Elmer MDL 1750 Fourier transform infrared spectrometer. Major bands were observed at 3400, 2980, 2960, 2930, 1700, 1636, 1618, 1264, 1153, 1070, 1040, 1006, 869 and 709 cm$^{-1}$.

Mass Spectral Data

The fast atom bombardment mass spectrum recorded on a Finnegan MAT90 instrument indicates a molecular weight of 902 (observed(M+H) at m/z 903 and (M+Na) at m/z 925). When combined with $^{13}$C-NMR data, the data indicates an empirical formula of $C_{47}H_{66}O_{17}$. The electron impact mass spectrum of the pertrimethylsilylated derivative showed characteristic fragmentation ions at m/z 617, 383 and 253.

The compound is soluble in organic solvents such as methanol, ethanol, dimethylformamide, dimethylsulfoxide and the like.

The compound of this invention has antifungal properties against both filamentous fungi and yeasts. Some of the filamentous fungi against which it is especially useful include *Alternaria solani, Cercospora beticola, Cochliobolus miyabeanus, Scopulariopsis communis, Ustilago zeae*, Penicillium sp., Phoma sp., *Rhizomucor miehei*, Trichoderma sp. Some of the yeast against which it is especially useful include *Candida albicans, Candida tropicalis, Candida rugosa, Cryptococcous laurentii, Saccharomyces cerevisiae* and the like.

Compound I is also useful as an agent for the treatment of *Pneumocystis carinii*, the causative agent of a pneumonia of particular severity to immune compromised patients such as those with acquired immune deficiency syndrome.

The use of Compound I as an antifungal agent and as an agent for the treatment of or for the prevention of *Pneumocystis carinii* infections also constitute aspects of the present invention.

PRODUCTION

The compound of the present invention, Compound I, is conveniently produced by cultivating *Dictyochaeta simplex*, also identified as *Codinaea simplex*, retained in the Merck Culture Collection as MF5247 and which has been deposited under the Budapest Treaty in the Culture Collection of the American Type Culture Collection at 12301 Parklawn Drive, Rockville, Md. 20852 and has been assigned the accession number ATCC 20960.

The colonial and morphological description of *Dictyochaeta simplex* ATCC 20960 are set forth below:

Colonies on cornmeal agar effuse, appressed, minutely tomentose, velvety, or pruinose, slightly convex in side view, up to 15 μm in diameter in 7 days, olive-gray, olive-black, pale to dark grayish black, Dark Greenish Olive, Dark Olive, Dark Grayish Olive, Olivaceous Black, Mineral Gray, Smoke Gray (capitalized color names from R. Ridgway, "Color Standards and Nomenclature", Washington, D.C. 1912).

Mycelium slightly immersed in the agar, septate, branched, 1-5 um wide, hyaline to gray brown or olive gray in KOH. Septae absent. Conidiophores arising directly from the vegetative mycelium, macronematous or mononematous, 23-140×3-5 um, simple or rarely branched, straight to slightly flexuous, 0-4 septate, cylindrical or sometimes tapered at point of attachment to vegetative mycelium, sometimes inflated towards apex, often with successive proliferations, thin-walled to slightly thick-walled hyaline to pale olive brown in KOH. Conidiogenous cells phialidic, intergrated, with terminal or lateral collarettes. Collarettes shallowly cylindrical to nearly hemispherical, up to 4 μm wide×2.5 μm deep, thin-walled, hyaline. Conidia 13-19.5-×3-4.5 μm, with two setulae, narrowly crescent-shaped to fusiform with, smooth-walled, aseptate, with finely granular cytoplasm, hyaline to pale grayish yellow in KOH. Setulae at distal ends of conidia, straight to slightly curved, hyaline, 3-6 μm long.

Although the production of the novel compound is discussed hereinbelow principally with respect to a specific strain, all strains of the genus ATCC 20960 and mutants are contemplated within the scope of this invention.

Compound I may be produced by cultivating *Dictyochaeta simplex* in a suitable nutrient medium under conditions hereinafter described and thereafter extracting the active component from the fermentation medium with a suitable solvent, concentrating the solution containing the desired component, then subjecting the concentrated material to chromatographic separation to separate Compound I from other metabolites also present in the cultivation medium.

The nutrient medium suitable for carrying out the fermentation contains sources of carbon and nitrogen assimilable by the microorganism and also contains low levels of inorganic salts. In addition, the medium may be supplemented with trace metals, although if complex sources of carbon and nitrogen are employed, they are usually present in the complex sources.

The ultimate medium may be solid or liquid, however, a liquid seed medium is usually first employed and the growth therefrom is used to inoculate production media.

Two seed media frequently employed are the following:

| KF Seed Medium | | HL Seed Medium | |
|---|---|---|---|
| | g/L | | g/L |
| Tomato paste | 40.0 | $KH_2PO_4$ | 15.0 |
| Corn steep liquor | 5.0 | Cerelose | 20.0 |
| Oat flour | 10.0 | Ardamine PH* | 1.0 |
| Cerelose | 10.0 | Pharmamedia** | 15.0 |
| Trace element mix | 10.0 ml | Lactic acid (85%) | 2.0 ml |
| presterile pH | 6.8 | Trace element mix | 10.0 ml |
| | | presterile pH | 7.0 |

| Trace Element Mix | |
|---|---|
| | g/L |
| $FeSO_4.7H_2O$ | 1.0 |
| $MnSO_4.4H_2O$ | 1.0 |
| $CuCl_2.2H_2O$ | 0.025 |
| $CaCl_2.2H_2O$ | 0.1 |
| $H_3BO_3$ | 0.056 |
| $(NH_4)_6Mo_7O_{24}.4H_2O$ | 0.019 |
| $ZnSO_4.7H_2O$ | 0.2 |
| in 1 liter 0.6NHCl | |

*yeast autolysate; Yeast Products, Inc., Clifton, NJ
**nonhydrolysed globular protein from cottonseed; Traders Protein, Buckeye Cellulose Corp., Memphis, Tenn.

The seed media are autoclaved for 20 minutes at 121° C. and 15 psi prior to use.

In the production media, the sources of carbon include glycerol, sugars, starches and other carbohydrates, or carbohydrate derivatives such as dextran, cerelose, as well as complex nutrients such as oat flour, corn meal, millet, corn and the like. The exact quantity of the carbon source which is utilized in the medium will depend, in part, upon the other ingredients in the medium, but it is usually found that an amount of carbohydrate between 0.5 and 5 percent by weight of the medium is satisfactory. These carbon sources can be used individually or several such carbon sources may be combined in the same medium.

The sources of nitrogen include amino acids such as glycine, arginine, threonine, methionine and the like as well as complex sources such as yeast hydrolysates, yeast autolysates, yeast cells, tomato paste, soybean meal, casein hydrolysates, yeast extracts, corn steep liquors, distillers solubles, cottonseed meal, meat extract, and the like. The various sources of nitrogen can be used alone or in combination in amounts ranging from 0.2 to 90 percent by weight of the medium.

Among the nutrient inorganic salts, which can be incorporated in the culture media are the customary salts capable of yielding sodium, potassium, magnesium, ammonium, calcium, phosphate, sulfate, chloride, carbonate, and like ions. Also included are trace metals such as cobalt, manganese, iron, molybdenum, zinc, cadmium, and the like.

Representative production media include the following solid production media:

| Medium A | | Medium B | |
|---|---|---|---|
| | per 250 ml flask | | per 250 ml flask |
| Cracked corn | 10.0 grams | Millet | 15.0 grams |
| Base liquid | 10.0 ml | Base liquid | 10.0 ml |

| Base liquid | |
|---|---|
| | g/L |
| Ardamine PH | 0.2 |
| $KH_2PO_4$ | 0.1 |
| $MgSO_4.7H_2O$ | 0.1 |
| Na tartrate | 0.1 |
| $FeSO_4.7H_2O$ | 0.01 |
| $ZnSO_4.7H_2O$ | 0.01 |
| pH unadjusted | |

Prior to use, the medium is autoclaved for 15 minutes at 121° C. and 15 psi, then 15.0 ml of distilled water is added and the medium autoclaved for 20 minutes.

Liquid media also may be employed. Fermentation on a larger scale is generally more conveniently carried out employing a liquid medium. It has been found that although Compound I may be obtained by carrying out the cultivation in conventional media such as Medium C of the following composition:

| Medium C | |
|---|---|
| | g/L |
| Dextrose | 10.0 |
| Corn meal | 10.0 |
| Glycine | 2.0 |
| Pectin | 10.0 |
| Tomato paste | 5.0 |
| Cod liver oil | 2.0 ml |
| Na citrate | 2.0 |
| $(NH_4)_2.SO_4$ | 2.0 |
| $CoCl_2.6H_2O$ | 0.01 | they have not been suitable for good yield of the desired compound. However, by incorporating from about 4.5 to about 7.5 percent by weight of dextrose, good yields of Compound I may be obtained. Further, the incorporation also of a small amount of glycerol, of the order of about 0.5 to 1.5 percent by weight appears to have an additional beneficial effect. Thus, method and compositions for producing Compound I in liquid medium constitute an aspect of the present invention. Media which may be employed are given below. One preferred medium is Medium D.

| | g/L |
|---|---|
| Medium D | |
| Dextrose | 50.0 |
| Glycerol | 10.0 |
| Glycine | 2.0 |
| Lard water | 5.0 |
| Soybean meal | 5.0 |
| Na citrate | 2.0 |
| $K_2HPO_4$ | 2.0 |

|  | g/L |
| --- | --- |
| CoCl$_2$.6H$_2$O | 0.01 |
| P-2000 | 2.0 ml |
| Medium E | |
| Dextrose | 40.0 |
| Glycerol | 20.0 |
| Corn steep liquor | 5.0 |
| Glycine | 2.0 |
| Lard water | 5.0 |
| Pectin | 10.0 |
| Na citrate | 2.0 |
| (NH$_4$)$_2$.SO$_4$ | 2.0 |
| KH$_2$PO$_4$ | 2.0 |
| Medium F | |
| Dextrose | 50.0 |
| Glycerol | 10.0 |
| Corn Meal | 10.0 |
| Glycine | 2.0 |
| Pectin | 10.0 |
| Tomato paste | 5.0 |
| Cod liver oil | 2.0 ml |
| Na citrate | 2.0 |
| (NH$_4$)$_2$.SO$_4$ | 2.0 |
| CoCl$_2$.6H$_2$O | 0.01 |

In the preferred process for producing Compound I, a fermentation broth containing *Dictyochaeta simplex*, ATCC 20960 is prepared by inoculating spores or mycelia of the antibiotic-producing organism into a suitable medium and then cultivating under aerobic conditions.

The procedure generally is first to inoculate a preserved source of culture into a nutrient seed medium and to obtain, preferably through a two step procedure, growth of the organisms which serve as seeds in the production of the antifungal agent. After inoculation, the flasks are incubated with or without agitation at temperatures in the range of from about 15° to about 30° C., preferably 20° to 28° C. Agitation when employed, may be up to 400 rpm, preferably about 200 to 220 rpm. The incubation is carried out over a period of from 2 to 30 days, preferably 2 to 4 days. When growth is abundant, usually between 2 and 5 days, the culture growth may be used to inoculate the production medium for the production of the antifungal agent. A second stage fermentation may be carried out. If employed, a portion of the culture growth is employed with similar incubation condition but employing a shorter time.

After inoculation, the fermentation production medium is incubated for 3 to 30 days, usually 7 to 14 days, preferably with but also without agitation. The fermentation may be conducted aerobically at temperatures ranging from about 20° C. to about 40° C. and agitation may be at a rate of 200 to 500 rpm. For optimum results, the temperatures are in the range of from about 24° C. to about 30° C., most preferably from about 24° C. to 28° C. The pH of the nutrient medium suitable for producing the instant compound is in the range of from about 5.0 to 8.5, preferably about 6.0 to 7.5. After an appropriate period for the production of the desired compound, the latter may be recovered as hereinafter described.

The active material may be recovered by the steps comprising (1) adding alcohol to said medium, stirring, steeping and thereafter filtering to recover the active component in the resulting alcoholic solution; (2) adding water to the alcoholic solution to convert it to a primarily aqueous solution, or concentrating to remove part of the alcohol and optionally thereafter adding water or brine; (3) adding a water-immiscible oxygenated organic solvent such as an ester or ketone, to the aqueous solution and intimately contacting the liquid phases to extract or partition the active component into the water-immiscible solvent layer, and then separating and concentrating the non-aqueous solution; (4) subjecting the material recovered in Step (3) to adsorption chromatography or to a combination of adsorption and partition chromatography wherein in each chromatographic separation, the active component from the eluates exhibiting activity against *Candida pseudotropicalis* are combined and concentrated to recover Compound I.

The exact steps may vary somewhat depending on whether the fermentation had been carried out in liquid or solid medium, what solvent is employed and what adsorbent or combination of adsorbents is employed.

When the fermentation is carried out in solid medium, the first step may be carried out by adding an alcoholic solvent to the fermentation medium, thoroughly mixing, then filtering, recovering and concentrating the aqueous alcohol filtrate. The filtrate is extracted or partitioned with a water-immiscible oxygenated organic solvent or an aromatic or halogenated hydrocarbon solvent and the resulting water-immiscible solvent solution concentrated, loaded onto a column for at least one, generally several separation steps by adsorption chromatography which may be combined with partition chromatography.

When the fermentation is carried out in a liquid medium, the mycelial solids may be filtered and recovered from the fermentation medium. Alcohol is added to the mycelial cake, and the mycelial solid thoroughly mixed with the alcohol, filtered, and the filtrate collected and concentrated. Then in a manner similar to that described for isolation from solid media, the alcoholic aqueous solution is intimately admixed with a water-immiscible oxygenated organic solvent to extract or partition the product thereinto, and the resulting solution then employed in chromatographic separations.

The alcoholic solvent to be employed in the initial extraction of the active agent from the solid nutrient medium or from the mycelial pad may be any of the lower alcohols such as methanol, ethanol, isopropanol, and the like. Methanol is preferred.

The water-immiscible non-polar organic solvent useful for extracting or partitioning the active agent from the alcohol solution are esters, such as ethyl acetate, isopropyl acetate, butyl acetate and the like, and ketones, such as methyl ethyl ketone (butanone). Ethyl acetate or butanone is preferred.

The chromatographic separation may be carried out by employing conventional column chromatography with non-ionic resin. The fractions containing the antibiotic Compound I may be detected by bioautography using *Candida pseudotropicalis*.

Silica gel is the preferred adsorbent but may be alternated with other adsorbents. Various grades of silica gel and sizes of silica gel are available commercially (from E. Merck or as Kieselgel from E. M. Science). Other adsorbents such as alumina, styrene-divinylbenzene copolymers available commercially as Diaion HP-20, HP-30, HP-40 (Mitsubishi Chemical Industries, Ltd.) and Amberlite XAD-2, XAD-4, XAD-16 (Rohm and Haas Co.) also may be employed.

When silica gel is the adsorbent an alkanol/chlorohydrocarbon mixture such as methanol/methylene chloride is useful as an eluant.

The biologically active fractions then may be combined and applied to a preparative HPLC column for purification. The eluate may then be concentrated for recovery of the product which may be further purified by extraction with a ketone, drying first with $Na_2SO_4$ and then azeotroping with toluene.

The broad antifungal activity of the compound of the present invention may be seen from the results of a disk diffusion assay showing activity of Compound I against a variety of filamentous fungi and yeasts. The organisms used in such assays are filamentous fungi and yeasts. Stock cultures of fungi are maintained on potato dextrose agar (Fifco) and transferred serially at two week intervals using standard microbiological techniques. Yeasts are maintained frozen at $-80°$ C. in 20 percent aqueous glycerol.

Seeded agar assay plates are prepared according to the type of assay strain. Inoculum for filamentous fungi are prepared by scraping the surface of stock plates with a moistened sterile dacron swab. The spores and mycelia are then suspended in 10 milliliters of sterile potato dextrose broth (PDB) and adjusted to 70% transmittance (T) at 660 nm. Inoculum for yeasts are prepared from overnight broth cultures. Cultures are then diluted into PDB to a final concentration of either 40% or 70% T at 660 nm. Assay plates are prepared by diluting the inoculum into appropriate molten agar medium, cooled to 45° C., to yield a final concentration of 4%.

Samples are applied to 6.2 mm filter paper disks (25 $\mu$l/disk) and air dried at 24° C. The disks are then applied to seeded assay plates with sterile forceps, and rewetted with 25% sterile aqueous dimethyl sulfoxide (DMSO). The assay plates are then incubated at either 28° or 37° C. for 24 hours.

Following incubation, inhibition zones were measured and recorded. Measurements are made from the extreme edge of any zone where the growth differs from the background lawn. Inhibition zones are notes as to appearance: fuzzy—a zone that has a fuzzy edge and clear center surrounding the disc, hazy—a zone that is hazy throughout, slightly hazy—a zone in which low levels of growth are discernible throughout the inhibition zone, very hazy—a zone in which the differences between the background lawn and inhibition zone are barely discernible, and ringed—a zone of increased growth is visible at the edge of the zone.

The product of the present invention demonstrated a broad spectrum of antifungal activity in the foregoing tests. It is effective against filamentous fungi and against yeasts and shows some activity against some bacteria. Representative fungal organisms against which activity was seen include *Alternaria solani, Aspergillus flavus, Aspergillus fumigatus, Aspergillus niger, Cercospora beticola, Cochliobolus miyabeanus, Botrytis allii, Scopulariopsis communis,* Penicillium sp, Phoma sp, Trichoderma sp, *Candida tropicalis* and *Saccharomyces cerevesiae.*

Compound I is not only a broad antifungal agent but also has potent fungicidal properties, particularly against organisms causing mycotic infections, such as *Candida albicans* and *Candida tropicalis*. The superior properties for the treatment of mycotic infections may be illustrated with minimum fungicidal concentration (MFC) results in tests against the aforenamed organisms in a microbroth dilution assay employing as medium a Yeast Nitrogen Base (Difco) with 1% dextrose (YNBD) as the medium. In carrying out the assay, Compound I was solubilized in 10 percent dimethyl sulfoxide (DMSO) and diluted to 2560 $\mu$g/ml. The compounds were then diluted to 256 $\mu$g/ml in YNBD. Thereafter, 0.15 ml of the suspension was dispensed to the first row of a 96-well plate (each well containing 0.15 ml of YNDB) resulting in a final drug concentration of 128 $\mu$g/ml in the first wells of each row. Twofold dilutions were then made from the top row to obtain final drug concentrations ranging from 128 to 0.06 $\mu$g/ml.

The yeast cultures, maintained on Sabouraud dextrose agar were transferred to YM broth containing yeast extract, malt extract, peptone and dextrose, from Difco) and incubated overnight at 35° C. with shaking (250 rpm). After incubation, each culture was diluted in sterile water to yield a final concentration of $1-5\times10^6$ colony forming units (CFU)/ml.

96-well microplates were inoculated using a MIC-2000 (Dynatech) which delivers 1.5 $\mu$l per well yielding a final inoculum per well of $1.5-7.5\times10^3$ cells. The microplates were incubated at 35° C. for 24 hours. The minimum inhibitory concentrations (MICs) were recorded as the lowest concentrations of drug showing no visible growth.

After recording the MIC, the plates were shaken to resuspend the cells. Thereafter, 1.5 $\mu$l samples from the wells in the 96-well microplate were transferred to a tray containing Sabouraud dextrose agar. The inoculated trays were incubated 24 hours at 28° C. and then read for minimum fungicidal concentration (MFC). The MFC is defined as the lowest concentration of drug showing no growth or less than 3 colonies per spot.

Against seven strains of *C. albicans,* the MFC was from 1.0 to 2.0 $\mu$g/ml and against *C. tropicalis* it was 1.0 $\mu$g/ml.

The antifungal properties of the present invention may be effectively utilized by administering an antifungal amount of Compound I to the area, object or subject on or in which control of fungi is desired. The amount of Compound I to be employed depends on the particular fungal organism to be controlled and the particular environment in which it is to be administered.

From the various test results, it is determined that for therapeutic antifungal use generally from about 10 to about 100 mg/kg of body weight of the Compound 1 may be employed while considering the patient's health, weight, age and other factors which influence response to a drug. These amounts when expressed as doses suitable for human beings are in the range of from about 500 mg to about 5000 mg daily by oral or parenteral administration.

Compound I is also useful against *Pneumocystis carinii* infections particularly troublesome among immune compromised patients such as those with acquired immune deficiency syndrome. Effectiveness against *P. carinii* may be demonstrated in a study involving mice.

In a representative study, ten male C3H/Hej mice, weighing 22-24 gms. each, were immunosuppressed by the addition of dexamethasone to the drinking water (8.0 mg/L) for six weeks to induce the development of *P. carinii* infections. To enhance the infection the mice were also maintained on a low protein diet. At the beginning of the seventh week the mice were divided into two groups. Both groups continued to receive dexamethasone in the drinking water and low protein diet for the remainder of the study. Mice in Group I were injected intraperitoneally twice daily with 0.5 ml of a 10% DMSO solution as a vehicle control. Mice in Group II were injected intraperitoneally twice daily with 0.5 ml of sterile water containing 0.0625 mg of Compound I (dissolved in DMSO, final concentration of DMSO is 10%, actual dose was 2.5 mg/kg). The treatment period lasted one week.

At the end of the treatment period (a total of seven weeks immunosuppression) the animals were sacrificed and the lung tissue removed. The tissue was then processed to determine the number of cysts for each animal. Compound I reduced the number of cysts by 93% as compared to the control animals.

From the foregoing test results and from known dosage ranges for trimethoprim-sulfamethocazole (TMP-SMZ) as applied to man, it is determined that generally to either treat or prevent Pneumocystis carinii infections from about 0.5 to about 20.0 mg/kg of body weight of Compound I may be employed while considering the patients' health, weight, age and other factors which influence response to a drug as well as whether it is to be applied to a human patient or to an animal. These amounts, when expressed as doses suitable for human beings, are in the range of from about 35 mg to about 1500 mg daily preferably by parenteral administration.

The antifungal or antipneumocystis properties are most effectively utilized when Compound I is formulated into a treating composition with a biologically inert carrier which in cases of use for pharmaceutical applications should also be pharmaceutically acceptable.

The compositions are formulated according to conventional compounding techniques with a biologically inert carrier, generally with the aid or a surface active dispersing agent, the nature of which would vary depending on whether the use is for the control of pathogens infecting man or animals, or in the case of fungi, whether it be for control of fungi in agriculture such as in soil or plant parts, or for the control of fungi in or on inanimate objects.

The novel compositions preferably contain 5 percent or more by weight of the active compound. Concentrate compositions may contain 15 percent or more and if for non-therapeutic use up to 90 percent or more. In preparing the compositions, Compound I is intimately admixed with an appropriate conventional carrier.

For non-therapeutic applications, the product of the present invention, either singly or as a mixture, may be employed in compositions in an inert-carrier which includes finely divided dry or liquid diluents, extenders, fillers, conditioners and excipients, including various clays, diatomaceous earth, talc, and the like, or water and various organic liquids such as lower alkanols, for example ethanol and isopropanol, or kerosene, benzene, toluene and other petroleum distillate fractions or mixtures thereof.

for therapeutic or medical applications, the compounds may be admixed with a pharmaceutically acceptable carrier, the nature of which will vary to some extent on whether the composition is to be topical, parenteral or oral.

For oral administration, the compound may be employed with a carrier which includes liquids such as water, glycols, oils, alcohols and the like which may have added buffering agents, sodium chloride, dextrose and various suspending, stabilizing solubilizing or dispersing agents. Solid carriers include starches, sugars, kaolin, ethyl cellulose, calcium carbonate, sodium carbonate, calcium phosphate, kaolin, talc, lactose, lubricants such as calcium stearate, binders, disintegrating agents and the like.

For parenteral applications, the compounds may be formulated in conventional parenteral solutions such as 0.85 percent sodium chloride or 5 percent dextrose in water or other pharmaceutically acceptable compositions.

For topical applications, the drug may be formulated in conventional creams and ointments such as white petrolatum, anhydrous lanolin, cetyl alcohol, cold cream, glyceryl monostearate, rose water and the like. Usually a 5 percent cream or solution is prepared and applied to the area to be treated.

it is especially advantageous to formulate the compositions in unit dosage form for ease of administration and uniformity of dosage. compositions in unit dosage form constitute an aspect of the present invention. The term "unit dosage form" refers to physically discrete units, each unit containing a predetermined quantity of active ingredient calculated to produce the desired therapeutic effect in association with the pharmaceutical carrier. Examples of such unit dosage form are tablets, capsules, pills, powder packets, wafers, measured units in ampoules or in multidose containers and the like. A unit dosage of Compound I may contain from 500 to 5000 milligrams for antifungal use and from 35 to 1500 milligrams for antipneumocystis use.

These compositions are then administered in amounts sufficient to obtain the desired antifungal, antipneumocystis or other antibiotic effect. For therapeutic application, the method comprises administering to a subject in need of treatment a therapeutically effective antifungal amount of Compound I. The appropriate dose will vary depending on age, severity, body weight and other conditions. For internal administration the composition may be applied by injection or administered orally. For topical application, it is applied at the site where control is desired. It may further be applied by other delivery methods such as transdermal delivery or insufflation.

The following examples illustrate the invention but are not to be construed as limiting.

EXAMPLE I

Solid Fermentation

A culture received as a soil tube was used in the fermentation. One glass scoopful of soil was inoculated into a 250 ml Erlenmeyer flask containing 50 ml of KF seed medium. The seed flask was then incubated for 48 hours at 26° C. at 220 rpm at 85% humidity.

The seed flask was then used to inoculate production media. Two types of production flasks were prepared: (1) forty non-baffled 250-milliliter Erlenmeyer flasks and (2) four 2-liter non-baffled Erlenmeyer flasks.

The smaller production flasks were prepared by adding 10.0 milliliters of base liquid to 10.0 grams of cracked corn and autoclaving for 15 minutes at 121° C. and 15 psi, adding 15.0 milliliters of distilled water and then autoclaving for 20 minutes at 121° C. and 15 psi.

The 2-liter flasks were prepared by adding 80 milliliters of base liquid to 80.0 grams of cracked corn per 2-liter flask. The flasks were then sterilized by autoclaving for 15 minutes at 121° C. and 15 psi, then 120 milliliters of distilled water was added to each flask, and thereafter again autoclaved.

Each seed flask was used to inoculate ten 250 milliliter flasks and one 2-liter flask by aseptically transferring 2.0 milliliters of seed growth to the 250 milliliter flask and 16 milliliters of seed growth to the 2-liter flask. All production flasks were then incubated at 26° C., 85% humidity. Eight of the 250 milliliter flasks, i.e., two of the flasks inoculated from each seed, were incubated statically while the remaining were incubated at 220 rpm. In all cases, the incubation time was fourteen days.

The production flasks were harvested by extracting the contents of the flasks with 65 percent methanol (45 milliliters for the 250 milliliter flasks and 360 milliliters for the 2 liter flasks), manually breaking eh mycelial growth and subsequently agitating the flasks for 60 minutes at 220 rpm.

Isolation

About 2 liters of the 65 percent methanol (MeOH) extract above-obtained was concentrated to 1 liter by vacuum evaporation. The aqueous residue (1 liter) was diluted with saturated brine solution (1 liter) and extracted into 2-butanone. The butanone extract was concentrated to dryness in vacuo and contained 2.1 gram of total solids. The residue was dissolved in 5/95 MeOH/$CH_2Cl_2$ and applied to a silica gel chromatography column (30 ml of Kieselgel 60, 0.040–0.063 mm). The column was eluted using a stepwise gradient consisting of 5/95 MeOH/$CH_2Cl_2$ (240 ml), 7.5/92.5 MeOH/$CH_2Cl_2$ (75 ml), 10/90 MeOH/$CH_2Cl_2$ (240 ml), 20/80 MeOH/$CH_2Cl_2$ (60 ml), and 100% MeOH (240 ml). Fractions of 6 ml were collected. The strongest biological activity eluted in the 10/90 MeOH/$CH_2Cl_2$ (fractions 66–95). These fractions were combined and concentrated to yield 221 mg of residue.

This rich cut was reconstituted in 2 ml of 46/54 acetonitrile/10 mM potassium phosphate buffer pH 6.5 and applied to a preparative HPLC column (Whatman Magnum 9 $C_{18}$ 9.4 mm ID×50 cm, 8 ml/min, 46/54 acetonitrile/10 mM potassium phosphate buffer pH 6.5). The most potent biologically active fraction (4 ml) eluted between 18.0 minutes and 18.5 minutes and was diluted with water (4 ml) and extracted into 2-butanone (8 ml). The organic layer was dried ($Na_2SO_4$) and the solvent was removed in vacuo and dried by azeotroping with toluene to yield 23 mg of a white solid.

The solid was soluble in methanol, 2l-butanone, and hot acetone but practically insoluble in water and toluene. The dried solid had a melting point of 168°–173° C. (with decomposition). The UV spectrum (MeOH) exhibited $\lambda_{max}$ at 262 nm ($\epsilon=29,700$), 240 nm ($\epsilon=23,700$) and a shoulder at 230 nm ($\epsilon=21,600$).

This product has the $^1H$ NMR, $^{13}C$ NMR, IR spectra, and mass spectral data previously detailed. medium, thoroughly mixing

EXAMPLE II

Liquid Fermentation

A frozen vial culture (2.0 milliters) of *Dictyochaeta simplex* maintained in the Merck Culture Collection as MF5247 was used to inoculate 50 milliliters of KF seed medium in a 250 milliliter unbaffled Erlenmeyer flask. The seed flasks were then incubated for 72 hours at 26° C., 200 rpm and 85 percent humidity. In the second stage seed culture, 10 milliliters of inoculum were transferred into each of four 2-liter unbaffled Erlenmeyer flasks containing 500 milliliters of KF seed medium. The seed flasks were incubated at 26° C., 180 rpm and 85 percent humidity for 48 hours.

Two liters of the second state seed culture were used to inoculate each of two 50 liters of production media contained in Chemap fermentors. The production medium was of the following composition: Cerelose 55.0 g/liter, Glycerol 10.0 g/liter, Glycine 2.00 g/liter, lard water 5.0 g/liter, Soybean meal 5.0 g/liter, $KH_2PO_4$ 2.0 g/liter, $CoCl_2 \cdot 6H_2O$ 0.01 g/liter, Sodium citrate 2.0 g/liter and Polypropylene glycol P2000 antifoam (Dow Chemical Co.) 2.0 ml/liter. The pre-sterile pH was adjusted to 7.0 with NaOH and the fermentations were carried out at 26° C. with an airflow of 15 liters per minute and impeller speed of 400 rpm for 192 hours. At the end of the cultivation period, the two media were combined for isolation of Compound I.

Isolation 100 liters of whole broth from the foregoing 8 day submerged fermentation was placed in a high speed centrifuge to separate the mycelia. An HPLC analysis of the centrifuged broth compared to a previously prepared sample of Compound I showed that less than 5 percent of the desired compound was present and the centrifuged broth was discarded.

The mycelial cake which amounted to 1.2 kg was extracted twice by stirring overnight each time with 4 liters of 80/20 MeOH/$H_2O$. The extracts were filtered through celite to obtain 8 liters of 80/20 MeOH/$H_2O$ extract which was calculated to contain 160 grams of total solids and about 10 grams of the desired Compound I.

Four liters of hexane was intimately contacted with the methanol/water extract above obtained, the layers separated and the hexane layer discarded. Four liters of saturated NaCl solution was added to the extract and the resulting solution extracted three times with 6 liters of methylene chloride. The methylene chloride extracts were combined, dried over anhydrous sodium sulfate and concentrated to recover about 80 grams of dark residue.

The residue was dissolved in methanol and adsorbed onto about 400 grams of silica gel. The methanol was removed in vacuo. The residue coated silica gel was then applied to the head of a silica gel chromatography column (1.5 liters of Kieselgel 60), packed in methylene chloride. The column was eluted at 20 milliliters/minute using a stepwise gradient of $CH_2Cl_2$ (3 liters), 5/95 MeOH/$CH_2Cl_2$ (1.3 liters), 7.5/92.5 MeOH/$CH_2Cl_2$ (1.2 liters), 10/90 MeOH/$CH_2Cl_2$ (2.5 liters), 15/85 MeOH/$CH_2Cl_2$ (1 liter). Fractions of about 500 milliliters each were collected. The fractions were assayed by thin layer chromatography using previously obtained Compound I as standard (TLC conditions: Whatman $KC_{18}F$, 80/20, MeOH/50 mM potassium phosphate buffer pH 7.2, $R_f$ 0.32, UV and $I_2$ detection). Compound I was found to be in the 10/90 MeOH/$CH_2Cl_2$ eluate fractions. The fractions were combined and concentrated to obtain 6.2 grams of dark residue.

The residue was dissolved in about 20 milliliters of methanol and added to 40 milliliters of 50 mM $KHPO_4$ pH 6.5 buffer at the head of a reverse phase flash chromatography column (50 ml of Baker octadecyl, 0.040 mm). The column was eluted at 5 ml/min using a stepwise gradient consisting of 33/67 MeOH/$H_2O$ (100 ml), 50/50 MeOH/$H_2O$ (200 ml), 60/40 MeOH/$H_2O$ (200 ml), 65/35 MeOH/$H_2O$ (200 ml), 70/30 MeOH/$H_2O$ (200 ml), 80/20 MeOH/$H_2O$ (200 ml) and 100% MeOH (200 ml). Ten milliliter fractions were collected. Compound I was obtained between the 60 percent and 70 percent fractions. The fractions were concentrated and combined to obtain 3.1 grams of a tan solid.

39 milligrams of the solid was reconstituted in 2 milliliters of 46/54 acetonitrile/water and applied to a preparative HPLC column (Whatman Magnum 20 C$_{18}$ 22 mm ID×25 cm) and eluted with 46/24 acetonitrile/water at 10 milliliters/minute. The fractions eluting between 32 and 39 minutes were combined, and the solvent removed in vacuo to obtain 23 milligrams of a white solid having indentical $^1$H-NMR and UV spectra as the previously identified and characterized material.

EXAMPLE III

The following are representative formulations containing Compound I:

Formulation A 1000 compressed tablets each containing 500 milligrams of Compound I are prepared from the following formulation:

|  | Grams |
| --- | --- |
| Compound I | 500 |
| Starch | 750 |
| Dibasic calcium phosphate hydrous | 5000 |
| Calcium stearate | 2.5 |

The finely powdered ingredients are mixed well and granulated with 10 percent starch paste. The granulation is dried and compressed into tablets.

Formulation B 1000 hard gelatin capsules, each containing 500 milligrams of Compound I are prepared from the following formulation.

|  | Grams |
| --- | --- |
| Compound I | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

Formulation C 250 milliliters of an injectable solution are prepared by conventional procedures having the following formulation:

| Dextrose | 12.5 grams |
| --- | --- |
| Water | 250 milliliters |
| Compound I | 400 milligrams |

The ingredients are blended and thereafter sterilized for use.

Formulation D

An aerosal composition is prepared of the following components:

|  | Per Canister |
| --- | --- |
| Compound I | 24 mg |
| Lecithin, NF liquid concentrate | 1.2 mg |
| Trichlorofluoromethane | 4.025 g |
| Dichlorodifluoromethane | 12.15 g |

What is claimed is:

1. A compound having the formula

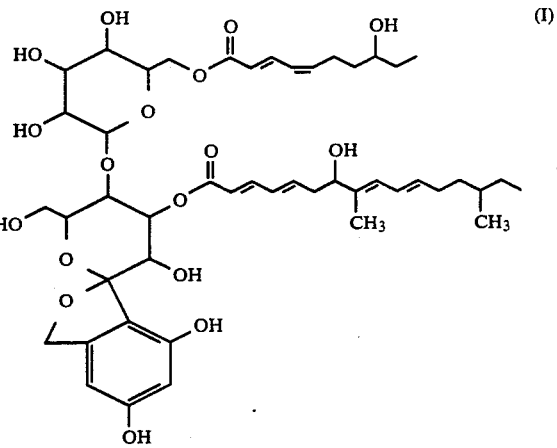

and named 3',4',5',6'1-tetrahydro-3',5,7-trihydroxy-6'1-(hydroxymethyl)-5'-[[tetrahydro-3,4,5-trihydroxy-6-[[(8l-hydroxy-1-oxo-2,4-decadienyl)oxy]methyl]-2H-pyran-2-yl]oxy]spiro[isobenzofuran-1(3H),2'-[2H]pyran-4'-yl]71-hydroxy-8,141-dimethyl-2,4,8,10-hexadecatetraenoate.

2. An antibiotic composition comprising the compound of claim 1 in admixture with a pharmaceutically acceptable carrier.

3. An antibiotic composition in unit dosage form which comprises per dosage unit from about 35 to 5000 milligrams of the compound of claim 1.

4. A composition according to claim 3 which is an antifungal composition in which the dosage unit amount is from about 500 to about 5000 milligrams.

5. A composition according to claim 3 which is an antipneumocystis composition in which the dosage unit amount is from about 35 to about 1500 milligrams.

6. A method for treating mycotic infections comprising administering an antifungally effective amount of the compound of claim 1.

7. A method according to claim 6 in which the amount of the compound is from about 10 to about 100 mg/kg of body weight.

8. A method for the treatment of or for the prevention of *Pneumocystis carinii* infections in mammals which comprises administering to mammals an anti-infective amount of the compound of claim 1.

9. A method according to claim 8 in which the amount of the compound is from about 0.5 to about 20.0 mg/kg of body weight.

* * * * *